United States Patent

Mui et al.

[11] Patent Number: 5,882,636
[45] Date of Patent: Mar. 16, 1999

[54] PHTHALATE FREE NAIL POLISH ENAMEL COMPOSITION

[75] Inventors: Ronnie F. Mui, Reading, Pa.; Thomas R. Candia, Cedar Grove, N.J.; James F. Joyce, Flemington, N.J.; Eric P. Wimmer, Princeton, N.J.

[73] Assignee: Tevco, Inc., South Plainfield, N.J.

[21] Appl. No.: 897,178

[22] Filed: Jul. 21, 1997

[51] Int. Cl.⁶ .............................. A61K 7/04; A61K 7/043
[52] U.S. Cl. ................. 424/61; 424/401; 106/3; 434/100
[58] Field of Search .......... 424/61, 401; 106/3; 434/100

[56] References Cited

U.S. PATENT DOCUMENTS

| | | |
|---|---|---|
| 4,097,589 | 6/1978 | Shansky . |
| 4,222,908 | 9/1980 | Ikeda et al. . |
| 4,649,045 | 3/1987 | Gaske et al. . |
| 5,066,484 | 11/1991 | Castrogiovanni et al. . |
| 5,093,108 | 3/1992 | Pappas et al. . |
| 5,133,966 | 7/1992 | Khanns et al. . |
| 5,145,670 | 9/1992 | Castrogiovanni et al. . |
| 5,145,671 | 9/1992 | Castrogiovanni et al. . |
| 5,174,996 | 12/1992 | Weber et al. . |
| 5,180,847 | 1/1993 | Thurman et al. . |
| 5,210,066 | 5/1993 | Sakuri et al. . |
| 5,225,185 | 7/1993 | Castrogiovanni et al. . |
| 5,227,155 | 7/1993 | Castrogiovanni et al. . |
| 5,277,899 | 1/1994 | McCall . |
| 5,290,543 | 3/1994 | Ounanian et al. . |
| 5,523,076 | 6/1996 | Schoon . |
| 5,599,530 | 2/1997 | Patil et al. . |
| 5,601,808 | 2/1997 | Mellul et al. . |
| 5,607,665 | 3/1997 | Calello et al. . |
| 5,681,550 | 10/1997 | Rubino . |
| 5,792,447 | 8/1998 | Socci et al. . |

*Primary Examiner*—Thurman K. Page
*Assistant Examiner*—Brian K. Seidleck
*Attorney, Agent, or Firm*—Craig M. Bell; Dann, Dorfman, Herrell and Skillman

[57] ABSTRACT

A phthalate-free long-lasting nail polish enamel composition consisting essentially of a film-forming agent, solvents, one or more colorants, one or more suspending agents, adhesion promoters and plasticizers selected from the group consisting essentially of the adipates, pentaerythrityl tetrabenzoate, 2,2,4-trimethyl-1,3-pentanediol diisobutyrate, pentaerythrityl tetraacetate and mixtures thereof. Preferably, the nail composition is free of any toluene-containing components as well.

7 Claims, No Drawings

PHTHALATE FREE NAIL POLISH ENAMEL COMPOSITION

FIELD OF INVENTION

The present invention relates generally to the area of cosmetics and cosmetic formulations for external use on the body; more particularly, the present invention relates to novel long lasting nail polishes, lacquers or enamels.

BACKGROUND OF THE INVENTION

Cosmetics and their use as decorative applications for the human body have been in existence for centuries and are used extensively throughout the world. A multibillion dollar industry, cosmetics perform many different functions from lipstick to eyeliner, facial creams, powders, highlighters and nail polishes or lacquers. Although they are used primarily by women, their use is extraordinary and has made many of the cosmetic producing and marketing firms very profitable endeavors.

The nail polish sector of the cosmetic industry is extremely competitive and new colors, combinations and variations thereof are constantly being introduced in an attempt by the formulator to get and hold onto a bigger piece of the market share. The scientific research that is poured into these endeavors is considerable and new products and/or brand names are continually being introduced.

Nail polishes are essentially comprised of pigments and/or dyes that are incorporated and suspended in various solvents and bases. They must also be stabilized in suspension since if during the shelf life of the product the pigments should float, settle, separate or striate the product's appearance will be adversely affected. Nail polishes should also be formulated so that the film formed thereby is tough and durable and adheres to the human nail and will not readily crack, chip, peel or splinter when worn. This toughness should last for an extended time as well so that the polish enamel is durable.

Nail enamels conventionally comprise a film forming component, which is frequently nitrocellulose, cellulose acetate butyrate, or a combination of one or both of those cellulosics with a polyurethane or other polymeric compound. Nail enamels have also traditionally included plasticizers, typically a phthalate such as dibutyl phthalate, or camphor, and have also typically included as an adhesion promoter, a polymeric component formed by the condensation polymerization of formaldehyde or other aldehyde, typically an aromatic sulfonamide-aldehyde condensation resin such as o, p-toluene sulfonamide formaldehyde resin, or a polyester resin such as phthalic anhydride trimellitic anhydride/glycol copolymer.

It has very recently become desirable to produce a nail enamel with reduced amounts of phthalate and aldehyde (e.g., formaldehyde) condensation products, in order to alleviate concerns that some wearers may be sensitized to these compounds or uncondensed aldehyde in the nail enamel. It is also desirable to reduce any volatile components since the volatility results in a loss of the component through evaporation which causes variability in the performance of the nail enamel. However, attempts to formulate such nail enamels have encountered difficulties because the nail enamel's desired properties such as long wear, high gloss, resistance to chipping on the nail, and compatibility with other nail enamel ingredients, are sensitive to changes in the ingredients in the nail enamel and to changes in the amounts of those ingredients. Therefore, there is still a need for a nail enamel formulation exhibiting satisfactory properties and containing little or no phthalate and/or aldehyde condensation products.

The prior art concerning nail enamels and/or lacquers strives to provide a nail enamel that exhibits superior suspension and stability characteristics for long shelf life duration as well as a high gloss, brilliant color and sheen that won't chip or crack during use and will withstand household chemical and temperature environments.

U.S. Pat. No. 5,066,484 to Castrogiovanni et al discloses and claims a number of glycerol triesters useful as plasticizers in nail polish compositions. The formulation further comprises a film-forming component, a solvent, pigments and other optional compounds as is known in the art. U.S. Pat. No. 5,145,670 also to Castrogiovanni et al. discloses similar nail compositions comprised of glycerol triacetates and trioctanoates as the plasticizers of choice. U.S. Pat. No. 5,225,185 also to Castrogiovanni et al. similarly discloses novel nail lacquers in which the formulation is free of formaldehyde and phthalate and the plasticizer is comprised of a copolymer formed by the condensation polymerization of formaldehyde and/or other aldehyde, typically an aromatic sulfonamide-aldehyde condensation resin. U.S. Pat. No. 5,227,155 also to Castrogiovanni et al. discloses further improved nail lacquers with glycerol triacetylricinoleate and glycerol tribenzoate as the plasticizers.

U.S. Pat. No. 5,133,966 to Khamis discloses still further nail polish formulations comprising improved pigment suspension systems. More specifically, the suspensions comprise carboxylic acids and their salts with a resin carrier in a buffered coating process that allegedly yields a hydrophobic coating with increased dispersion characteristics. Surprisingly, these suspensions allegedly don't effect the uniform dispersion of the pigments or the gloss and color of the nail polish enamel. U.S. Pat. No. 5,174,996 to Weber et al. discloses nail enamels with improved floatation, migration and settlement characteristics. These improved features are achieved by coating the pigments with oxidized polyethylene.

None of the prior art nail polish compositions have been able to exhibit a high gloss, defined color, long wear and chip resistance and yet retain nail flexibility and adherence over extended periods of time. More specifically, none of the prior art formulations achieve this goal while at the same time providing a phthalate-free plasticizer that, during wear, retains its durability and prevents the enamel from hardening and becoming more brittle which invariably results in the cracking and breaking of the nail coating.

SUMMARY OF THE INVENTION

The improved nail enamels and/or lacquers of the present invention are free of phthalates, and preferably other organic solvents such as toluene, yet exhibit superior shelf life stability, wear life and durability through the incorporation of preferably three, but depending on the formulation as many as ten novel plasticizers and adhesion promoters that are highly shelf stable and promote a superior film coating on the nail.

DETAILED DESCRIPTION OF THE INVENTION

Whereas typical nail polish or enamel formulations incorporate nitrocellulose as the primary film forming agent, the tensile strength and the adhesive qualities of the enamel for the nail surface are generally inferior if nitrocellulose is used without plasticizers. The other ingredients in the nail enamel formulations known in the art, i.e., plasticizers, resins, pigments and thixotropic agents are added as needed depending upon the particular application to which the nail enamel is intended.

Nail enamels must be durable to resist physical and harsh household chemical attack and must also be flexible since the human nail is pliable and grows with time. Hence, to improve the tensile strength and adhesion characteristics of nail enamels, plasticizers and resins have generally been added to the nitrocellulose film forming composition.

Dibutyl phthalate has been used as the plasticizer of choice for many years since it provides excellent flexibility, elongation and tensile strength to nail polish formulations, there are now concerns that it may generate toxic side effects to the wearer and may raise environmental concerns at the industry level. Therefore, it would be extremely beneficial if replacement plasticizer compositions could be found that are free of phthalate and do not raise the same toxic and environmental concerns, are compatible and stable with the other ingredients found in nail polish composition and yet still afford the superior durability and flexible necessary for a long lasting nail color and sheen.

The nail polish compositions of the present invention are necessarily phthalate free, they may or may not contain some residual toluene, depending on the formulation desired. Preferably, the compositions are both phthalate and toluene free, however some formulations provide superior durability and flexibility with minor amounts of toluene added. Otherwise the nail polish enamel compositions of the present invention are comprised of conventional ingredients; i.e., nitrocellulose as a primary film forming agent, acrylate copolymers may be added as a secondary film forming agent; ketones such as methyl ethyl ketone, isopropyl alcohol, diacetone, ethyl or butyl acetate as solvents and optionally, toluene as a solvent, phthalic anhydride/ trimellitic anhydride/glycol copolymers and tosylamide formaldehyde resins as adhesion promoters and any one or more of a countless number of F. D. & C. colorants useful as colors for the composition. The plasticizer which gives the superior performance of the enamel of the present invention is selected from the group consisting of:

1. An adipate
2. Pentaerythrityl tetrabenzoate
3. 2,2,4-trimethyl-1,3-pentanediol diisobutyrate Preferably, dioctyl adipate is the plasticizer of choice and is incorporated in the nail enamel formulations of the present invention in amounts of from 0.1 to 15.0 weight percent (wt %) based on the total weight of the enamel composition. Structurally, dioctyl adipate (Bis[2-ethylhexyl] adipate) is represented by the chemical formula:

2,2,4-Trimethyl-1,3-pentanediol diisobutyrate (TXIB) is a second plasticizer that is extremely effective in producing nail enamels that are both flexible durable and long lasting. It is represent by the structural formula:

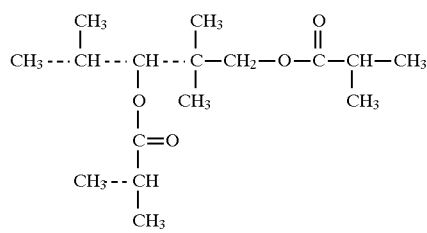

Pentaerythrityl tetrabenzoate is a third preferred plasticizer represented by the structural formula:

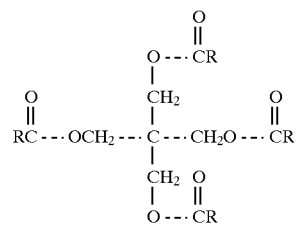

Wherein R is a benzyl.

This plasticizer also acts as an adhesion promoter and flow aid.

Whereas the prior three plasticizers have been found to comprise the preferred embodiments of the present invention, a number of other adipates and pentaerythrityl tetraacetate may be substituted therefore and still afford superior nail enamel coatings. These include the following:

a. Diisobutyl Adipate
b. Dipropyl Adipate
c. Diisostearyl Adipate
d. Diisocetyl Adipate
e. Diisodecyl Adipate
f. Diisononyl Adipate
g. Pentaerythrityl Tetraacetate These other plasticizers are incorporated in the nail enamel formulations of the present invention in the same amounts (0.1–15.0 wt %) as the first three enumerated above. Preferably, a combination of two or more of these plasticizers will be employed in the nail enamels of the present invention.

The remaining ingredients in the novel nail enamel formulations of the present invention include those compounds well known in the nail polish industry. A film forming agent is necessary in order to provide the nail enamel with a consistency that results in the formulation of a uniform, stable film on the surface of the nail when the enamel is applied thereon. Nitrocellulose is the preferred film former and must be incorporated in the formulation in amounts that will cause the enamel to readily spread out about the surface of the nail yet remain viscous enough to not run or drip therefrom. However, it must also readily cling to and flow from the applicator brush as the enamel is applied from bottle to nail and this generally comprises from about 5.0 to 40 wt % of the total weight of the composition and preferably will be incorporated in amounts of from about 3 to about 30 wt %. Other suitable, but not preferred film formers include cellulose acetate butyrate, polyurethanes, and mixtures thereof.

The solvent components are selected to be as inert to the user's nail and to the other components of the nail enamel composition as possible. It should also be capable of dissolving or dispersing the other components so that they readily flow onto the nail. The solvent must be able to evaporate from the nail in a matter of minutes at room temperature and pressure so that the film forming agents, plasticizers and other components dissolved therein solidify and adhere to the nail surface. Examples of preferred solvents include isopropanol, butyl acetate, ethyl acetate, propyl acetate, and mixtures thereof. Effective amounts of the solvent component will generally lie in the range of about 30 wt % to about 70 wt % of the composition.

A suspending agent is an optional, but preferred component of the nail enamel compositions of the present invention. The suspending agent should help suspend the pigments in the nail enamel, and helps adjust the viscosity of the enamel to achieve desired flowability. Examples of preferred suspending agents include montmorillonite clays, and treated clays such as stearalkonium hectorite which are preferred. The amount of the suspending agent can of course depend on the desired flow characteristics of the nail enamel, but amounts on the order of about 0.2 to about 2.0 wt % are generally satisfactory.

The nail enamel compositions of the present invention can be clear, i.e. unpigmented, or they can include a pigment component. Suitable pigments include the inorganic and organic pigments which are useable in cosmetic formulations. Particular examples include titanium dioxide, D&C Red #6 Barium Lake, D&C Red #7 Calcium Lake, D&C Red #34 Calcium Lake, FD&C Yellow #5 Aluminum Lake, Ferric Ferrocyanide, Red Iron oxide, Black Iron Oxide, Mica, Bismuth Oxychloride, Guanine, D&C Red #17, D&C Red #33, D&C Violet #2, D&C Yellow #11, FD&C Blue #1 and FD&C Green #3.

The term "pigment" includes mixtures of one or more of the foregoing compounds. These pigments can be surface treated for even better performance. See U.S. Pat. Nos. 5,133,966 to Khamis; 4,832,944 to Socci et al. and 5,174,996 to Weber et al., all of which are hereby incorporated herein by reference.

The amounts of any particular ingredients comprising the pigment component will of course depend on the shade desired by the practitioner. In general, the pigment component comprises about 0.01 to about 15.0 wt % of the composition.

Nail enamels in accordance with the present invention can be manufactured by thoroughly and intimately mixing together all the components indicated above, in the amounts described above. Examples of satisfactory equipment and how to use it are readily apparent to one of ordinary skill in the art.

The mixing procedure for the nail enamel formulations of the present invention is as those generally known in the art wherein the film-forming component is first mixed into the solvent, followed by the plasticizer and then the other ingredients, always while mixing.

The nail enamel formulation of the present invention, as stated before, provides a superior long-lasting color and gloss that is chip resistant, durable, flexible and will withstand harsh household chemicals, adverse temperatures and the effects of other external factors for long periods of time.

The following examples are provided to more specifically define the formulations of the present invention and to disclose preferred embodiments of the nail enamels. They are presented for illustrative purposes only and it is recognized that there are minor changes and alterations that can be made with respect to the ingredients and/or their amounts not disclosed herein. It should be understood that to the extent any such changes do not materially affect the final composition or its functionality, they are considered to fall within the spirit and scope of the invention as later recited in the claims.

EXAMPLE I

A nail polish enamel base was formulated without the added plasticizers of the present invention comprising the following ingredients. The values given represent weight percentages based on 100%

| | |
|---|---|
| Butylacetate (solvent) | 6.4633 wt % |
| Propylacetate (solvent) | 3.7625 wt % |
| Ethylacetate (solvent) | 30.0255 wt % |
| Butyl alcohol (solvent) | 1.0303 wt % |
| Sucrose Benzoate | 0.9355 wt % |
| Nitrocellulose (film former) | 18.0000 wt % |
| Sucrose acetate isobutyrate | 17.0000 wt % |
| Benzophenone-1 (U.V. light inhibitor) | 0.0468 wt % |
| Stearalkonium hectorite (suspending agents) | 18.7101 wt % |
| Citric acid (10% in isopropyl alcohol) | 0.2339 wt % |
| Styrene/acrylate/acrylonitrile copolymer | 0.3274 wt % |
| Acrylate copolymer | 0.4678 wt % |
| Phthalic anhydride/trimellitic anhydride/ glycol copolymer polyester resin | 2.7632 wt % |

EXAMPLE 2

The nail enamel base formulated in Example 1 was then prepared as five samples incorporated a plasticizer selected from the group comprising dibutyl phthalate (DBP), dioctyl adipate (DOA) and Bis(2-ethylhexyl) terephthalate (BET). The different samples were formulated as set forth below, the values given on a weight percent (wt %) basis.

| | Sample | | | | |
|---|---|---|---|---|---|
| | 1 | 2 | 3 | 4 | 5 |
| Base | 93.0 | 93.0 | 93.0 | 93.0 | 93.0 |
| Dibutyl phthalate | 7.0 | | | | |
| Dioctyl adipate | | 7.0 | 5.77 | 5.25 | 4.2 |
| Bis(2-ethyl-hexyl terephthalate) | | | 1.23 | 1.75 | 2.8 |
| | 100 wt % | 100 wt % | 100 wt % | 100 wt % | 100 wt % |

Each sample was tested for hardness as is known in the art. The samples were drawn on a 4"×7" glass plate, allowed to dry and then subjected the Persoz Hardness test at various time intervals as shown below. The number of pendulum swings was recorded as shown.

| | Time Interval (in hours) | | | | | | | |
|---|---|---|---|---|---|---|---|---|
| Sample Type | 24 | 48 | 72 | 96 | 160 | 112 | 216 | 400 |
| Base Alone | 214 | 244 | 286 | 296 | 328 | 350 | 375 | 381 |
| Sample 1 | 89 | 89 | 107 | 102 | 110 | 114 | 102 | 119 |
| Sample 2 | 84 | 87 | 87 | 83 | 80 | 86 | 80 | 85 |
| Sample 3 | 93 | 98 | 94 | 95 | 92 | 98 | 93 | 96 |
| Sample 4 | 99 | 105 | 106 | 103 | 104 | 108 | 99 | 97 |
| Sample 5 | 108 | 97 | 121 | 116 | 118 | 119 | 112 | 111 |

As the data indicates, the nail enamel base alone without any plasticizer added was very hard and resulted in a nail coating that became extremely brittle and cracked. Sample 1 consisting of the dibutyl phthalate plasticizer with the base generated a more durable, pliable nail polish but again, this is a phthalate-containing composition. Sample 2, consisting of the dioctyl adipate plasticizer also gave similar results to the phthalate containing samples (1,3,4 and 5) i.e., a durable flexible "softer" polish that does not change or vary to any great degree over time. But surprisingly, sample 2 is phthalate-free. Moreover, this composition (#2) exhibited the same superior adhesion and flexibility characteristics after 400 hours as it did at 24.

EXAMPLE 3

| Copper Nail Enamel | |
|---|---|
| Butyl Acetate | 24.0700 wt % |
| Propyl Acetate | 3.2800 wt % |
| Ethyl Acetate | 29.9300 wt % |
| Sucrose Benzoate | 1.0000 wt % |
| Nitrocellulose | 14.0900 wt % |
| Isopropyl alcohol | 6.5600 wt % |
| Stearakonium Hectorite | 1.2900 wt % |
| Styrene/Acrylate/Acrylonitrile Copolymer | 0.2900 wt % |
| Acrylate Copolymer | 1.5400 wt % |
| Phthalic Anhydride/Trimellitic Anhydride/Glycol Copolymer | 1.9400 |
| D&C Red #6 Ba Lake | 0.1300 |
| Black Iron Oxide | 0.0700 |
| Bismith Oxychloride | 0.5500 |
| Iron Oxide Red | 0.0900 |
| D&C Red #7 Calcium Lake Lt. | 0.0100 |
| Dioctyl Apipate | 7.0000 |
| Sucrose Acetate Isobutyrate | 8.1600 |
| | 100.0000 |

| Mauve Nail Enamel | |
|---|---|
| Butyl Acetate | 20.000 wt % |
| Propyl Acetate | 3.500 wt % |
| Ethyl Acetate | 35.100 wt % |
| Nitrocellulose | 16.000 wt % |
| Isopropyl alcohol | 4.951 wt % |
| Stearakonium Hectorite | 1.000 wt % |
| Styrene/Acrylate/Acrylonitrile Copolymer | 0.500 wt % |
| Acrylate Copolymer | 1.000 wt % |
| Phthalic anhydride trimellitic Anhydride/Glycol Copolymer | 3.500 wt % |
| D&C Red #6 Ba Lake | 0.128 wt % |
| Titanium Dioxide | 0.426 wt % |
| Iron Oxide Black | 0.067 wt % |
| Iron Oxide Red | 0.096 wt % |
| D&C Red #7 Calcium Lake Dark | 0.001 wt % |
| Dioctyl Adipate | 3.230 wt % |
| Pentaerythrityl Tetrabenzoate | 3.501 wt % |
| 2,2,4-Trimethyl-1,3-Pentanediol Diisobutyrate | 1.000 wt % |
| Sucrose Acetate Isobutyrate | 6.000 wt % |
| | 100.000 wt % |

EXAMPLE 5

| Ivory Nail Enamel | |
|---|---|
| Butyl Acetate | 20.000 wt % |
| Ethyl Acetate | 35.100 wt % |
| Nitrocellulose | 18.000 wt % |
| Isopropyl alcohol | 6.500 wt % |
| Stearakonium Hectorite | 0.800 wt % |
| Styrene/Acrylate/Acrylonitrile Copolymer | 0.400 wt % |
| Acrylate Copolymer | 1.200 wt % |
| Phthalic Anhydride/Trimellitic Anhydride/Glycol Copolymer | 4.000 wt % |
| Titanium Dioxide | 0.256 wt % |
| Iron Oxide Red | 0.003 wt % |
| FD&C Yellow #5 Aluminum Lake | 0.010 wt % |
| Dioctyl Adipate | 1.750 wt % |
| Pentaerythrityl Tetrabenzoate | 4.000 wt % |
| 2,2,4-Trimethyl-1,3-Pentanediol Diisobutyrate | 2.980 wt % |
| Sucrose Acetate Isobutyrate | 5.000 wt % |
| | 100.000 wt % |

When subjected to the same Persoz hardness test as set forth in Example 2 for samples 1–5, the formulations set forth in Examples 3–5 exhibited the same superior durability, adhesion and flexibility characteristics as Sample 2.

What is claimed is:

1. A phthalate and toluene-free, nail polish enamel composition consisting essentially of a film-forming agent, organic solvent, one or more coloring agents, a suspending agent, an adhesion promoter selected from the group consisting of phthalic anhydride/trimellitic anhydride/glycol copolymer, tosylamide formaldehyde resins and mixtures thereof and a plasticizer selected from the group consisting essentially of adipates, and mixtures thereof.

2. The nail polish of claim 1 wherein said adipates are selected from the group consisting of dioctyl adipate, diisobutyl adipate, diisostearyl adipate, diisocetyl adipate, diisodecyl adipate, diisononyl adipate and mixtures thereof.

3. The nail enamel composition of claim 2 wherein said film-forming agent is selected from the group consisting of nitrocellulose, cellulose acetate butylrate, polyurethanes and mixtures thereof.

4. The nail enamel composition of claim 3 wherein said plasticizer is incorporated in the formulation in an amount of from about 0.1 to 15.0 wt %.

5. The nail enamel composition of claim 4 wherein said solvent is selected from the group consisting essentially of butyl acetate, propyl acetate, ethyl acetate, isopropanol, butyl alcohol, and mixtures thereof.

6. The nail enamel composition of claim 5 wherein said suspending agent is selected from the group consisting essentially of stearalkonium hectorite, montmorillonite clays, treated clays and mixtures thereof.

7. The nail enamel compositions of claim 6 wherein said coloring agent is selected from the group consisting of D. & C. and, F.D. & C. colorants, inorganic pigments, organic pigments, mica, guanine and mixtures thereof.

* * * * *